United States Patent [19]

Geuder

[11] Patent Number: 5,693,013

[45] Date of Patent: Dec. 2, 1997

[54] APPARATUS FOR ASPIRATING LENS DEBRIS DURING CATARACT OPERATIONS

[75] Inventor: Volker Geuder, Heidelberg, Germany

[73] Assignee: Hans Geuder GmbH, Heidelberg, Germany

[21] Appl. No.: 547,042

[22] Filed: Oct. 23, 1995

[30] Foreign Application Priority Data

Jan. 26, 1995 [DE] Germany .................. 195 02 305.6

[51] Int. Cl.$^6$ ................................................ A61B 17/00
[52] U.S. Cl. ........................................................ 604/35
[58] Field of Search ................................ 604/22, 27, 35, 604/43, 65, 67, 107, 167; 606/107, 159, 167

[56] References Cited

U.S. PATENT DOCUMENTS

| | | | |
|---|---|---|---|
| 4,841,984 | 6/1989 | Armeniades et al. | 128/748 |
| 4,870,964 | 10/1989 | Bailey, Jr. et al. | 128/303.1 |
| 5,261,883 | 11/1993 | Hood et al. | 604/153 |
| 5,322,504 | 6/1994 | Doherty et al. | 606/167 |

FOREIGN PATENT DOCUMENTS

3713420A1  11/1988  Germany .
3234621C2  10/1989  Germany .

Primary Examiner—Manuel Mendez
Attorney, Agent, or Firm—Collard & Roe, P.C.

[57] ABSTRACT

An apparatus used during eye surgery for aspirating lens debris from a surgical site at an anterior chamber of the eye during a cataract operation. The apparatus includes a container of flushing liquid connected to a hose. A handpiece is provided which includes a double lumen cannula having a first lumen and a second lumen connected to the hose for delivering flushing liquid to the surgical site. An aspiration conduit is connected to the first lumen. A peristaltic pump is connected to the aspiration conduit for aspirating flushing liquid containing lens debris from the surgical site. The motor drives the peristaltic and a computer controls the rotational speed of the motor based on the preset vacuum rise rate. A ventilation valve is connected to the aspiration conduit between the double cannula and the peristaltic pump. The valve is selectively opened to admit air into the aspiration conduit. A pressure-measuring sensor is coupled to the aspiration conduit and an automatic vacuum reduction control is connected to the pressure-measuring sensor for controlling the ventilation valve. The automatic vacuum reduction control opens the ventilation valve to instantly reduce the vacuum level. This occurs when the vacuum reaches or exceeds a predetermined vacuum change rate due to a clog in the aspiration conduit.

4 Claims, 2 Drawing Sheets

APPARATUS FOR ASPIRATING LENS DEBRIS DURING CATARACT OPERATIONS

BACKGROUND OF THE INVENTION

1. Field of the Invention

The present invention relates to an apparatus used during eye surgery for aspirating lens debris in cataract operations, during which a double-lumen cannula of a handpiece is inserted through a slit along the edge of the cornea of the eye into the anterior chamber of the eye. Flushing liquid is fed through one lumen of the cannula into the anterior chamber, and then aspirated together with lens debris via the other lumen of the cannula. Peristaltic pumps or pneumatically operated Venturi pumps are used as aspirators.

2. The Prior Art

An apparatus of this type with a peristaltic pump has been described in German Patent De-OS 3,234,621. With this apparatus, the suction capacity and/or the vacuum are infinitely variable via a foot switch. A device in the form of a pressure-measuring sensor is arranged between the pump and an aspiration hose connecting the pump with one lumen of a double cannula. The pressure-measuring sensor limits the suction effect of the pump to an adjustable level and is adjustable in steps to different pressures. The lumen is inserted into the anterior chamber of an eye undergoing surgery. The negative pressure limitation maintained by the pressure-measuring sensor assures that a preset vacuum is not exceeded when flushing liquid is aspirated together with the lens particles carried along by such liquid.

The prior art apparatus has been adequate, however, it is unsatisfactory to the extent that when the apparatus is put into operation, the adjusted vacuum builds up only very slowly. This results in an initial delay before the surgeon can start to remove lens debris.

On the other hand, apparatuses used during eye surgery equipped with Venturi pumps for aspirating lens debris are characterized by a very rapid development of a preset vacuum. However, such apparatuses have the drawback that the vacuum and the flow rate are directly dependent upon each other. The consequence thereof is that changes in the flow rate lead to different pressure conditions and hence to pressure variations in the anterior chamber of the eye undergoing surgery. Due to the changing requirement of infusion liquid in the anterior chamber, the infusion liquid source has to hang very high, which causes a very high volume of liquid to flow through the anterior chamber. Another important drawback of the apparatuses equipped with Venturi pumps is the compressed-air requirement of about 90 liters/minute at approximately 6 bar. Consequently, unsterile air escapes from such pumps in large amounts, which additionally causes highly undesirable eddying of the room air in the operating room.

SUMMARY OF THE INVENTION

It is therefore an object of the present invention to overcome the drawbacks of the prior art and to provide an apparatus for aspirating lens debris during cataract operation which rapidly develops a vacuum.

It is a further object of the present invention to provide such an apparatus with automatic vacuum reduction control.

These and other related objects are achieved according to the invention by an apparatus used during eye surgery for aspirating lens debris from a surgical site at an anterior chamber of the eye during a cataract operation. The apparatus includes a container of flushing liquid connected to a hose and a handpiece including a double lumen cannula comprising a first lumen and a second lumen connected to the hose for delivering flushing liquid to the surgical site. An aspiration conduit is connected to the first lumen and a peristaltic pump is connected to the aspiration conduit for aspirating flushing liquid containing lens debris from the surgical site. A motor drives the peristaltic pump with a computer controlling the rotational speed of the motor based on a preset vacuum rise rate. A ventilation valve is connected to the aspiration conduit between the double cannula and the peristaltic pump. The valve is selectively opened to admit air into the aspiration conduit. A pressure measuring sensor is coupled to the aspiration conduit and an automatic vacuum reduction control is connected to the pressure measuring sensor for controlling the ventilation valve. The automatic vacuum reduction control opens the ventilation valve to instantly reduce the vacuum level when the vacuum reaches or exceeds a predetermined vacuum change rate due to a clog in the aspiration conduit between the first lumen and the peristaltic pump.

An input unit is actively coupled to the computer to selectively predetermine the vacuum change rate at a nominal vacuum level. The device further includes a multifunction foot switch including a potentiometer having various positions. A first analog-to-digital converter is connected between the computer and the multifunction foot switch for transmitting the position of the potentiometer to the computer. Digital inputs/outputs are provided for the computer. The multifunction foot switch is connected to digital inputs/outputs for transmitting additional commands from the foot switch to the computer. A second analog-to-digital converter is connected between the computer and the pressure measuring sensor for digitizing an actual vacuum value signal measured by the pressure measuring sensor. A bargraph indicator is connected to the computer for visually displaying the actual vacuum values.

A digital-to-analog converter is connected to the computer for generating an analog signal representing a predetermined vacuum value. A control amplifier is connected to the digital-to-analog converter, the pressure measuring sensor and the motor. The control amplifier compares the analog signal to an actual vacuum value measured by the pressure measuring sensor and generates an output signal to control the motor. The output signal is proportional to the rotational speed of the pump.

In known apparatuses for aspirating lens debris, the peristaltic pump is driven at a constant rotational speed, so that flushing liquid is aspirated at a constant flow rate. Consequently there is no change in the volume of liquid used per unit time. With the apparatus according to the invention, the rotational speed of the pump is controlled depending on the preset vacuum rise rate, so that the desired vacuum is obtained within a selectable time. After the preset vacuum has been reached, the rotational speed of the pump is reduced in accordance with the desired flow rate of the liquid containing lens debris in the aspiration conduit. Such rotational speed of the pump is controlled via a foot switch in a manner known from DE-OS 3,713,420.

A measurement amplifier is connected between the pressure measuring sensor and the control amplifier for processing the nominal vacuum value signal generated by the pressure measuring sensor. A servo amplifier is connected between the control amplifier and the motor.

BRIEF DESCRIPTION OF THE DRAWINGS

Other objects and features of the present invention will become apparent from the following detailed description considered in connection with the accompanying drawings which disclose an embodiment of the present invention. It should be understood, however, that the drawings are designed for the purpose of illustration only and not as a definition of the limits of the invention.

In the drawings, wherein similar reference characters denote similar elements throughout the several views.

DETAILED DESCRIPTION OF THE PREFERRED EMBODIMENT

Figure 1:
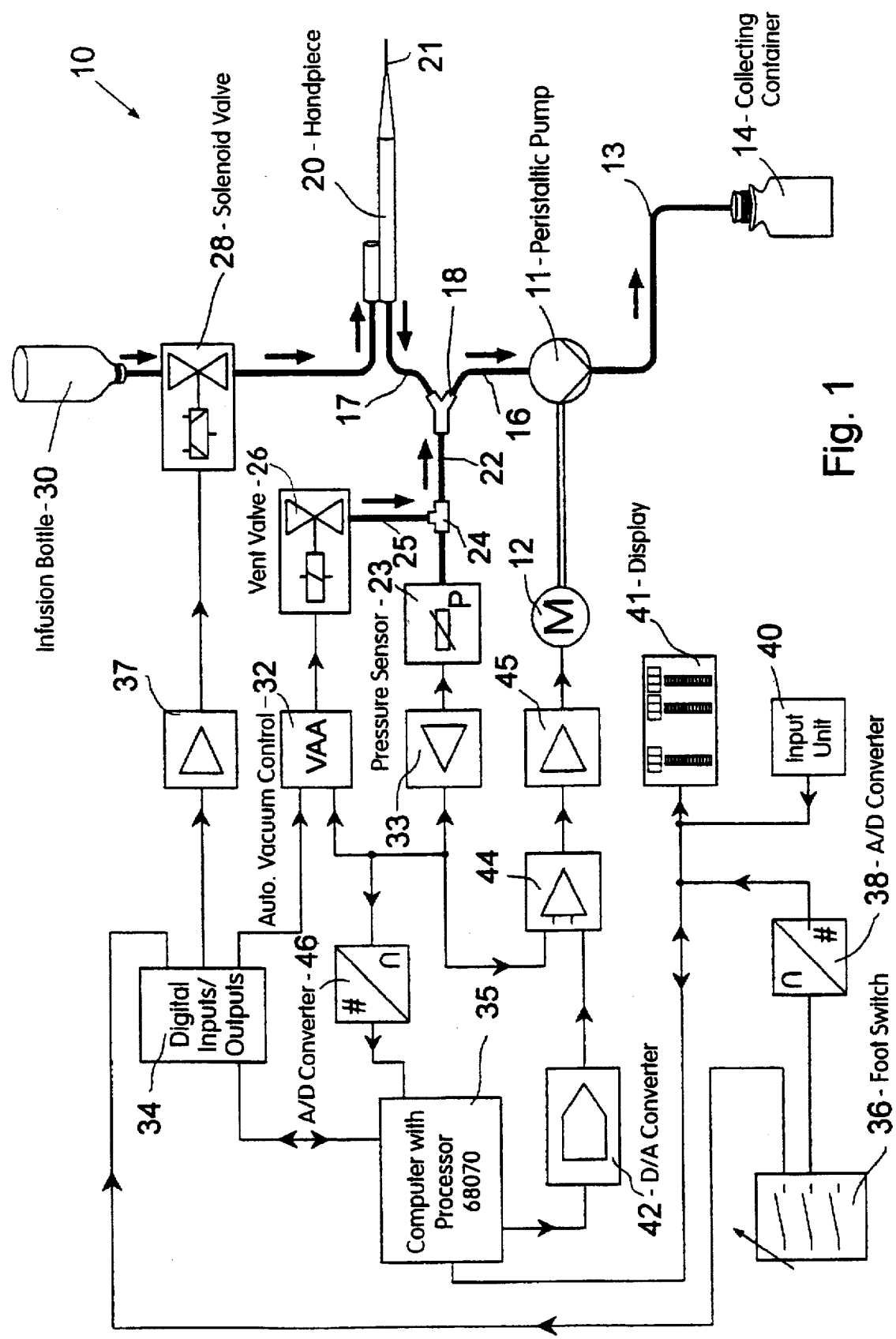
FIG. 1 is a schematic diagram of the apparatus according to the invention.

Turning now in detail to the drawings, FIG. 1 shows an apparatus 10 for aspirating lens particles during cataract operations equipped with a peristaltic pump 11 for producing a vacuum for aspirating flushing liquid loaded with lens particles from the anterior chamber of an eye undergoing surgery. The peristaltic pump 11 has a motor-driven rotary piston with at least two cams, which are displaced against each other in the circumferential direction. The two cams have the same angular spacing as each other. A peristaltic hose extends across a circumferential angle greater than the circumferential angle between the adjacent cams of the rotary piston. The peristaltic hose extends around the cams and is enclosed by a radial circumferential limitation.

As the rotary piston is revolving, sections of the peristaltic hose are forced by the cams of said piston against the circumferential limitation and progressively squashed off. The liquid volume present in the peristaltic hose ahead of the respective squashing site in the circumferential direction is passed on in the circumferential direction. This liquid contains the lens debris. The peristaltic pump 11 is driven by an electric motor 12, which is controllable by means of control electronics, which are described in greater detail below.

On the flow-off side, a conduit 13 extends from peristaltic pump 11 to a collecting container 14 for receiving the conveyed liquid and the lens debris carried along in such liquid. Furthermore, peristaltic pump 11 is connected with a handpiece 20 via an aspiration conduit consisting of the two conduit sections 16, 17, which are connected with each other via a branch fitting 18. The handpiece 20 has a double cannula 21 which, is inserted into the anterior chamber of the the eye through a slit on the edge of the cornea. Aspiration conduits 16 and 17 are connected with a pressure-measuring sensor 23 via branch fitting 18 and a conduit 22. The vacuum produced by peristaltic pump 11, as lens particles are being aspirated from the anterior chamber of an eye undergoing surgery, acts on pressure-measuring sensor 23. Finally, a ventilation valve 26, the function of which is explained in greater detail below, is connected with conduit 22 and consequently also with aspiration conduits 16 and 17 via a three-way fitting 24 arranged in conduit 22, and via another conduit 25.

One lumen of the double cannula 21 of the handpiece 20 is connected with the conduit section 17 of the aspiration conduit. Conduit section 17 is in connection with the pressure-measuring sensor 23 via the branch fitting 18. The second lumen of the double cannula 21 of the handpiece 20 is connected with a flushing liquid source 30 by means of a hose line 27. A solenoid valve 28 is installed within line 27 and is selectively switchted between a closed position and an open position. Flushing liquid source 30 may be a conventional infusion bottle suspended in a predetermined vertical position.

Furthermore, apparatus 10 comprises an automatic vacuum reduction control 32 for actuating the ventilation valve 26 when an impermissibly high rate of vacuum change occurs in the aspiration hoses 16 and 17. This may be the case when removing debris which clogs the lumen of the double cannula 21 of the handpiece 20 that is connected with aspiration hoses 16 and 17. Ventilation valve 26 is a solenoid valve. The automatic vacuum reduction control 32 is in switching connection with the pressure-measuring sensor 23 via a measurement amplifier 33. Automatic vacuum reduction control 32 is also connected to a computer unit 35 via the digital inputs/outputs 34. Furthermore, the apparatus 10 comprises a multifunctional foot switch 36, which is equipped with a potentiometer and actively connected via the digital inputs/outputs 34 and via a driver stage 37 with the solenoid valve 28 arranged in the hose conduit 27 for feeding flushing liquid.

Furthermore, the multifunctional foot switch 36 is actively connected via an analog-to-digital converter 38 with the computer unit 35, which in turn is connected with a keyboard for the input of a desired nominal vacuum value, and with an input unit 40 having the vacuum rise time.

Furthermore, via an analog-to-digital converter 46, the computer unit is connected between pressure-measuring senosr 23 and a bargraph indicator 41 for displaying the given actual value of the vacuum. By means of the analog-to-digital converter 46, the signals corresponding with the actual vacuum value measured by the pressure-measuring sensor 23 are transmitted to and processed by computer unit 35 in a way that they can be visually displayed by the bargraph indicator 41. These signals from pressure-measuring sensor 23 are processed by amplifier 33.

Depending on the value preset on the input unit 40 for the nominal vacuum value and the rate of vacuum rise, the computer unit 35 and a digital-to-analog converter 42 form a signal proportional to said values for controlling the driving motor 12. Digital-to-analog converter 42 is arranged downstream of the computer unit. This proportional signal is compared in a control amplifier 44, which is in signal connection with the pressure-measuring sensor 23 via the measurement amplifier 33. An output signal of the control amplifier 44 controls the driving motor 12 of the peristaltic pump 11 via a servo-amplifier 45.

Figure 2:
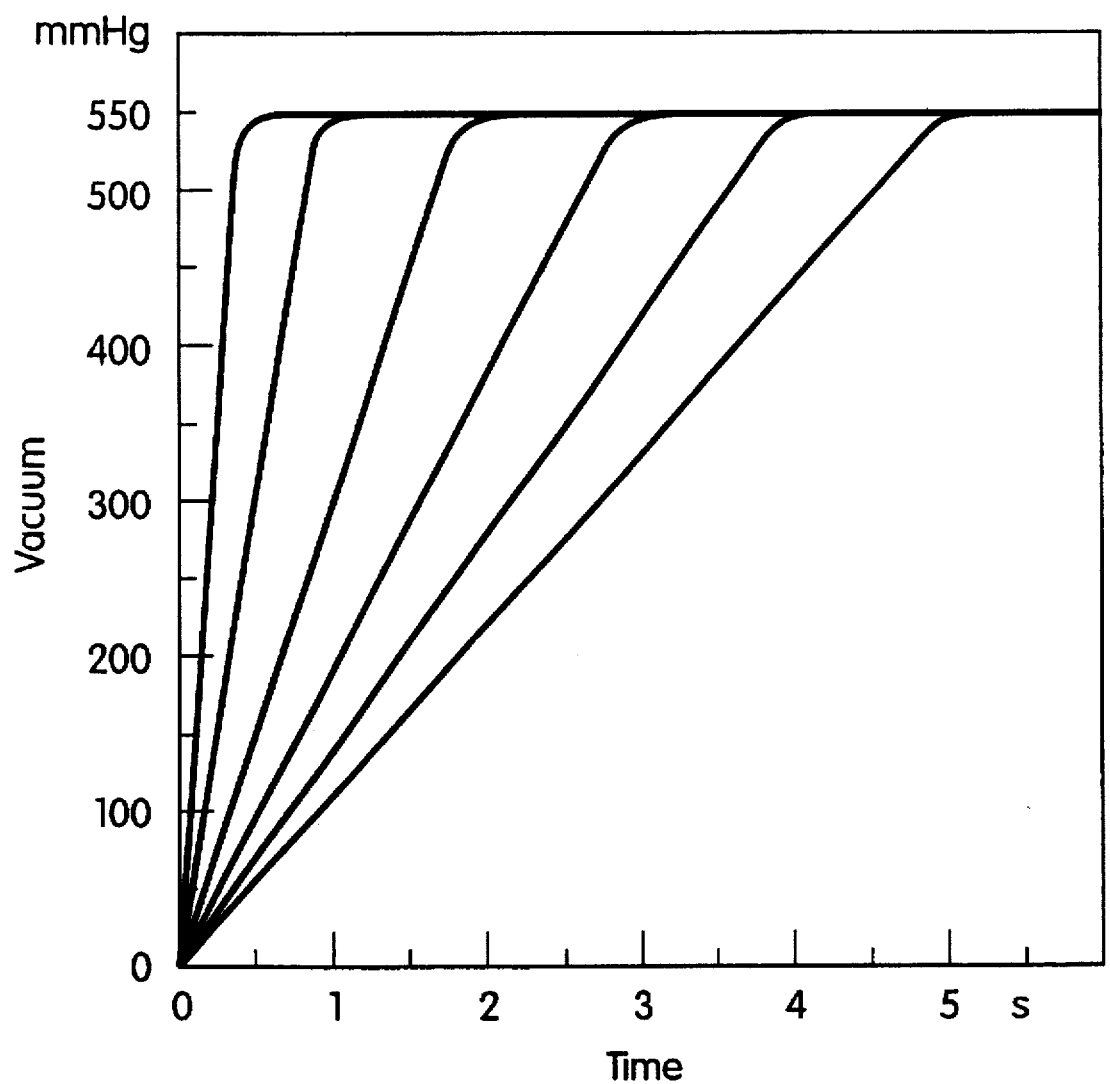
FIG. 2 is a graph illustrating the selectable vacuum rise when the apparatus is put into operation.

With the illustrated embodiment of the apparatus 10, the vacuum is infinitely variable between 0 and 550 mmHg. A total of six different vacuum rise rates is selectable, which is shown in FIG. 2, for a maximum nominal vacuum value of 550 mmHg. FIG. 2 also shows the sawtooth-like rise of the vacuum across time, which is totally different from the conventional course of peristaltic characteristics and approximates the characteristics of a Venturi pump.

After the apparatus has been readied for operation by means of a main switch (not shown for the sake of clarity), and following adjustment of the desired nominal vacuum value and adjustment of the desired rate of vacuum increase, the foot switch 36, which has a number of switching stages, is actuated first and set to a first stage. Solenoid valve 28 arranged in the feed conduit 27 between the flushing liquid source 30 and the handpiece 20, is initially closed when the apparatus is shut off, blocking the feed conduit 27. Solenoid valve 28 is switched open via the digital inputs/outputs 34 and the driver stage 37. This releases the feed of flushing liquid to the double cannula 21 of the handpiece 20.

By setting the foot switch to a second switching stage, the driving motor 12 and consequently the peristaltic pump 11 are put into operation via the analog-to-digital converter 38 and the computer unit 35, namely with a rotational speed conforming to the entered vacuum rise rate. The adjustment of the rotational speed of the driving motor 12 predetermines the rate at which the vacuum rises. Within the range of 0 and the preset nominal vacuum value, the desired vacuum is selected with the foot switch, which has a linear switching stage.

Heretofore, it has been typical of apparatuses of this type having peristaltic pumps that the vacuum builds up gradually, and that the vacuum desired for the aspiration process is obtained only after a predetermined time has elapsed. Consequently the full suction capacity is obtained only after such time has elapsed. In contrast thereto, a rapid rise in the vacuum is obtained when using Venturi pumps. Such preselectable rise in vacuum is illustrated in FIG. 2.

Multifunctional foot switch 36 has a further switching stage for reversing the direction of rotation of the driving motor. If clogging occurs in the suction system, for example within the zone of the aspiration opening of the lumen of the double cannula 21 that is connected with the aspiration conduit 16, 17, the direction of rotation of the driving motor and thus of the peristaltic pump is reversible. As a result that the build-up of pressure in the suction system is limited to a nominal value and the clogged site is flushed free.

While only a single embodiment of the present invention has been shown and described, it is to be understood that many changes and modifications may be made thereunto without departing from the spirit and scope of the invention as defined in the appended claims.

What is claimed is:

1. An apparatus used during eye surgery for aspirating lens debris from a surgical site at an anterior chamber of the eye during a cataract operation, comprising:

a container of flushing liquid connected to a hose;

a handpiece including a double lumen cannula comprising a first lumen and a second lumen connected to said hose for delivering flushing liquid to the surgical site;

an aspiration conduit connected to said first lumen;

a peristaltic pump connected to said aspiration conduit for aspirating flushing liquid containing lens debris from the surgical site;

a motor driving said peristaltic pump;

a computer controlling the rotational speed of said motor based on a preset vacuum rise rate;

a ventilation valve connected to said aspiration conduit between said double cannula and said peristaltic pump, said valve being selectively opened to admit air into said aspiration conduit;

a pressure-measuring sensor coupled to said aspiration conduit;

an automatic vacuum reduction control connected to said pressure-measuring sensor for controlling said ventilation valve;

wherein said automatic vacuum reduction control opens said ventilation valve to instantly reduce the vacuum level when the vacuum reaches or exceeds a predetermined vacuum change rate due to a clog in said aspiration conduit between said first lumen and said peristaltic pump;

an input unit actively coupled to said computer to select a predetermined vacuum change rate and a nominal vacuum level;

a multi-function foot switch including a potentiometer having a plurality of switching stages;

a first analog-to-digital converter connected between said computer and said multi-function foot switch for transmitting the switching stage of said potentiometer to said computer;

digital inputs/outputs provided for said computer, said multi-function foot switch being connected to said digital inputs/outputs for transmitting additional commands from said foot switch to said computer;

a second analog-to-digital converter connected between said computer and said pressure-measuring sensor for digitizing an actual vacuum value signal measured by said pressure-measuring sensor; and a bargraph indicator connected to said computer for visually displaying the actual vacuum values.

2. The apparatus of claim 1, comprising a digital-to-analog converter connected to said computer for generating an analog signal representing a predetermined vacuum value;

a control amplifier connected to said digital-to-analog converter, said pressure measuring sensor and said motor;

wherein said control amplifier compares the analog signal to an actual vacuum value measured by said pressure-measuring sensor and generates an output signal to control said motor, said output signal is proportional to the rotational speed of the pump.

3. The apparatus of claim 2, comprising a measurement amplifier connected between said pressure measuring sensor and said control amplifier for processing the nominal vacuum value signal generated by said pressure-measuring sensor.

4. The apparatus of claim 3, comprising a servo-amplifier connected between said control amplifier and said motor.

* * * * *